United States Patent
D'Ambrosio

(10) Patent No.: US 11,850,730 B2
(45) Date of Patent: Dec. 26, 2023

(54) DOUBLE EYE TRACKER CONFIGURATION FOR A ROBOT-ASSISTED SURGICAL SYSTEM

(71) Applicant: Asensus Surgical US, Inc., Durham, NC (US)

(72) Inventor: Andrea D'Ambrosio, Milan (IT)

(73) Assignee: Asensus Surgical US, Inc., Durham, NC (US)

( * ) Notice: Subject to any disclaimer, the term of this patent is extended or adjusted under 35 U.S.C. 154(b) by 239 days.

(21) Appl. No.: 16/932,658

(22) Filed: Jul. 17, 2020

(65) Prior Publication Data
US 2021/0039263 A1    Feb. 11, 2021

Related U.S. Application Data

(60) Provisional application No. 62/874,983, filed on Jul. 17, 2019.

(51) Int. Cl.
*B25J 13/08*    (2006.01)
*G06F 3/01*    (2006.01)

(52) U.S. Cl.
CPC .............. *B25J 13/08* (2013.01); *G06F 3/013* (2013.01)

(58) Field of Classification Search
CPC ........... B25J 13/08; G06F 3/013; A61B 34/30
USPC ........................................................ 700/264
See application file for complete search history.

(56) References Cited

U.S. PATENT DOCUMENTS

| | | | |
|---|---|---|---|
| 8,320,623 B2 | 11/2012 | Cleveland | |
| 8,734,326 B2 | 5/2014 | Finlay | |
| 9,176,580 B2 | 11/2015 | Moraviec | |
| 9,360,934 B2 | 6/2016 | Ruiz Morales et al. | |
| 9,639,953 B2 | 5/2017 | Moraviec | |
| 9,649,020 B2 | 5/2017 | Finlay | |
| 9,674,435 B1* | 6/2017 | Monari | H04N 5/23238 |
| 2004/0174496 A1* | 9/2004 | Ji | G06V 40/18 |
| | | | 351/209 |
| 2010/0168765 A1 | 7/2010 | Moraviec | |
| 2014/0285432 A1* | 9/2014 | Guez | A61B 34/25 |
| | | | 345/156 |
| 2017/0172675 A1 | 6/2017 | Jarc et al. | |
| 2017/0180720 A1* | 6/2017 | Jarc | G02B 27/017 |
| 2018/0074581 A1* | 3/2018 | Melman | G06T 7/74 |
| 2018/0330652 A1* | 11/2018 | Perreault | G09G 3/02 |

(Continued)

FOREIGN PATENT DOCUMENTS

WO    2015143073 A4    9/2015

OTHER PUBLICATIONS

Nyström M, Niehorster DC, Cornelissen T, Garde H. Real-time sharing of gaze data between multiple eye trackers—evalnation, tools and advice. Behav Res Methods. Aug. 2017;49(4):1310-1322. doi: 10.3758/s13428-016-0806-1. PMID: 27743316; PMCID: PMC5541105. (Year: 2017).*

(Continued)

*Primary Examiner* — Stephen S Hong
*Assistant Examiner* — Broderick C Anderson

(57) ABSTRACT

Eye gaze measurements are used to give input to a surgical robotic system. Eye tracking input is enhanced using a pair of eye trackers positioned to track the gaze of a user observing an endoscopic image on a display. At least one of the eye trackers is moveable relative to the display in a horizontal and/or vertical direction relative to the image display.

4 Claims, 3 Drawing Sheets

(56) References Cited

U.S. PATENT DOCUMENTS

2019/0339535 A1* 11/2019 Abi-Chaaya ....... G02B 27/0093
2021/0378757 A1* 12/2021 Bay ......................... G06F 3/011

OTHER PUBLICATIONS

Turner, Jayson, et al. "Extending the Visual Field of a Head-mounted Eye Tracker for Pervasive Eye-based Interaction." Proceedings of the Symposium on Eye Tracking Research and Applications, ACM, Mar. 2012, https://doi.org/10.1145/2168556.2168613. (Year: 2012).*

Kommu et al., "Initial experience with the EndoAssist camera-holding robot in laparoscopic urological surgery"; J Robotic Surg (2007) 1:133-137, Published Mar. 9, 2007.

* cited by examiner

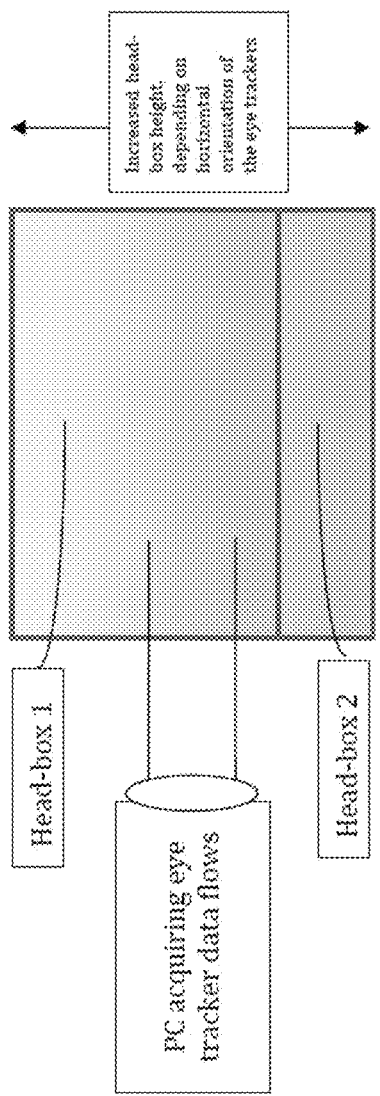
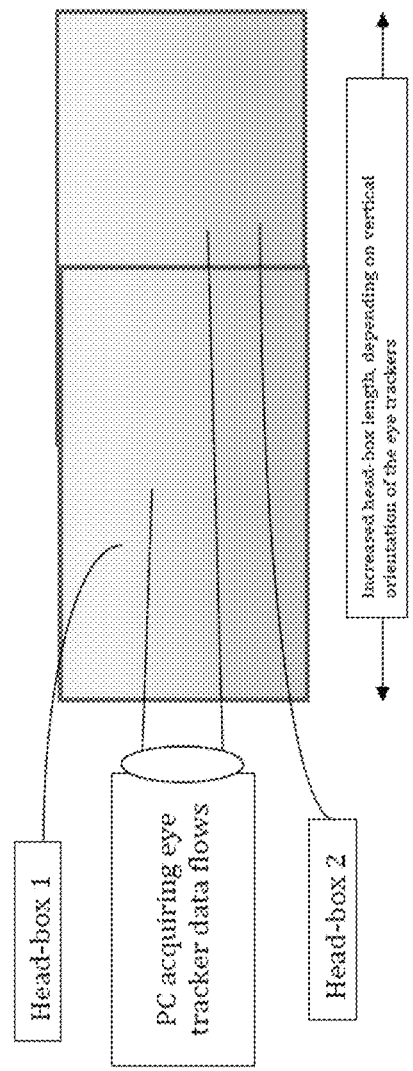

DOUBLE EYE TRACKER CONFIGURATION FOR A ROBOT-ASSISTED SURGICAL SYSTEM

This application claims the benefit of U.S. Provisional Application No. 62/874,983, filed Jul. 17, 2019

FIELD OF INVENTION

The present invention relates to a system and method that can be used to drive/control functions of a robotic application based on eye gesture/eye gaze. In particular, the invention relates to a system and method for measuring eye gaze/eye gesture as a form of user input to drive a function of a robotic system, such as the movement of a surgical instrument or endoscopic camera.

BACKGROUND

Human-computer interaction is one of the emerging technologies in the robotic application field, particularly in the robotic-assisted surgical procedures.

An effective human-computer interaction is based on measuring the behavior of the user's eye to control/drive an application/instruments. The eye behavior tracking involves measuring an eye gaze and estimating the point of interest and direction of the subject's gaze. The eye gaze estimation is an important process for ensuring accuracy in an eye gaze based human-computer interaction procedure.

U.S. Pat. No. 10,251,713, owned by the assignee of the present application and incorporated herein by reference, teaches a robotic surgical system configured to receive eye tracking input and, in response, causing movement of a manipulator arm holding the endoscopic camera, allowing repositioning of the camera using only eye movement. Eye tracking is used as input in a variety of other applications beyond surgical robotics, and the concepts described in this application may be us both within and outside the surgical robotics field. As described in that application, the eye tracking system comprises two cameras arranged alongside each other at a suitable distance so as to record two spatially offset pictures of the surgeon's eyes. Thus, an associated processor can perform a triangulation of the user's gaze direction depending on the comparison of the two recorded pictures.

The term "head box" refers to the volume inside which the head of the user must be positioned in order to be tracked by the eye-tracker. At times, eye tracking can be interrupted if the user moves his/her head out of the head box, thus impacting reliability of the system. The concepts described in this application are intended to improve eye tracking use by minimizing operational impacts caused by user head repositioning.

BRIEF DESCRIPTION OF THE DRAWINGS

FIG. 1 is schematic diagram of showing a frontal view of a vertical mounting configuration of a double connected architecture for eye trackers.

FIG. 2 is a schematic diagram showing a frontal view of a horizontal mounting configuration of double connected architecture for eye trackers.

DETAILED DESCRIPTION

Figure 3:
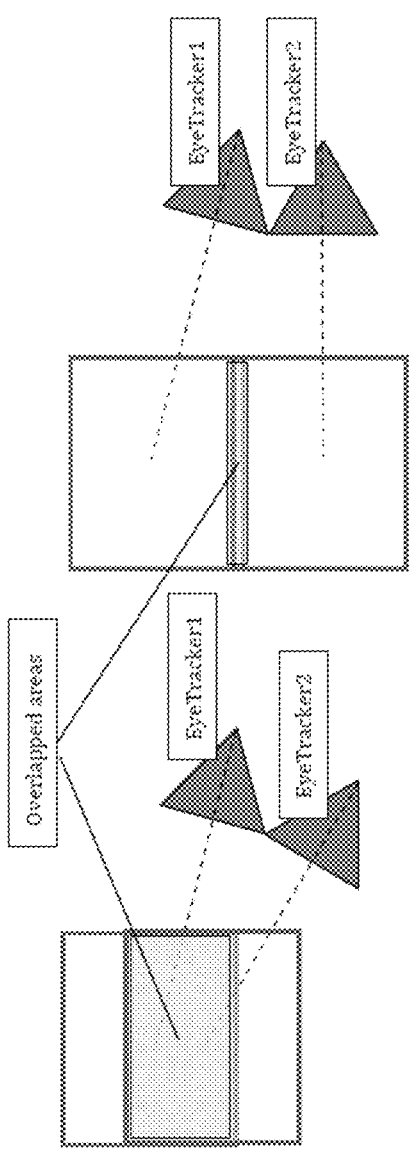
FIG. 3 is a schematic diagram showing a lateral view of a vertical configuration of a double connected architecture for eye trackers.

The disclosed embodiments will be described in the context of a surgical robotic system including:
  At least one robotic arm working in an operating theatre, holding a surgical instrument or a surgical endoscope.
  A surgeon console which includes but is not limited to: a 2D/3D image display, a user interface or haptic user interface that the user manipulates to give input to the system for movement and/or operation of surgical instruments held by robotic arms, an eye tracker device and a PC.
  2D or 3D vision system having an endoscopic camera that can acquire video from the surgical workspace.
  Software, or a software component stored in memory, executable to process data flow coming from the eye tracker device and control movement or operation of the camera. This may include sending movement commands to the arm which is holding the endoscopic camera. This functionality of driving the camera using eye gaze input could be replaced by a different way to move the camera. Camera drive can include panning movement in every direction, plus zoom in/zoom out movements. Eye tracking input may be additionally/alternatively used to pan or zoom the image without moving the manipulator supporting the camera, such as by articulating the camera itself, performing digital pan/zoom etc. In some implementation, camera drive functionality could also include a rotation of the endoscope, or the rotation of the tip of the endoscope. In some implementations, the eye tracker device may be used for other purposes, such as management of controls of the software interface of the surgeon console, and/or mean to set or adjust settings of the robotic system.

The disclosed system relies on a double connected eye tracker as a means to provide the system with two sources of information on factors such as position of eyes, gaze coordinates along the screen in front of the surgeon, distance between eyes and tracker. Such a configuration allows for a comparison of data with the purpose of identify the best data available for the calculations to be made using the eye gaze data. Furthermore, for eye trackers including a camera for user face recognition, the double source of such a profile could improve the quality of the recognition.

Embodiments of different architectures for double connected eye trackers, including vertical and horizontal configurations, are shown in the drawings.

In the embodiments shown in FIGS. 1 and 2, which schematically depict a frontal view of an eye tracker arrangement, the head-box positions depend on the mutual orientation of the frontal face of eye trackers. Different orientations means different height (or length, if horizontal) and consequently different areas of overlap regions for the head boxes. Either or both eye tracker may be moveable to allow changes in the size of the head box.

Referring to FIG. 3, an overlap zone is the volume where the eyes of the surgeon are tracked by both the eye trackers. The overlap zone allows redundant acquisition coming from both the devices. In this case, the parallel data flow is evaluated by a proper algorithm comparing corresponding data types. In some implementations, an indicator of quality coming from each eye tracker that indicates the goodness of the data source shall be available and the elaboration model evaluating the data comparison will use this indicator during the elaboration. In case of bad data from one of the eye trackers, the algorithm will consider as good value the one coming from the other eye tracker (redundancy).

When both the data values are good, a specific elaboration model shall calculate the best data resulting. When both data values are bad, the elaboration model calculates the best prediction or will instead alerts the user that eye tracker data is not available to the interface or can consider as acceptable the missing point from input data stream.

Figure 4:
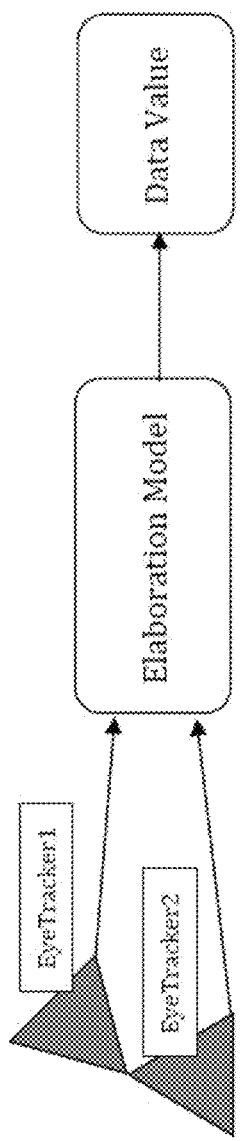
FIG. 4 is a schematic diagram of an eye tracker data processing module

FIG. 4 shows a process flow in which the model elaboration block, will include mathematical models and/or statistical models and/or learning algorithms and/or predictive models.

The connection of more than one eye tracker to the same PC, addresses a problem of interference between the IR signals emitted by each device reflected by each eye. To solve this issue, the application shall provide a mechanism of mutual exclusion of the illuminator included in each eye tracker during the IR emission and following receiving. The implementation of this synchronizing mechanism could be done in different ways.

Figure 5:
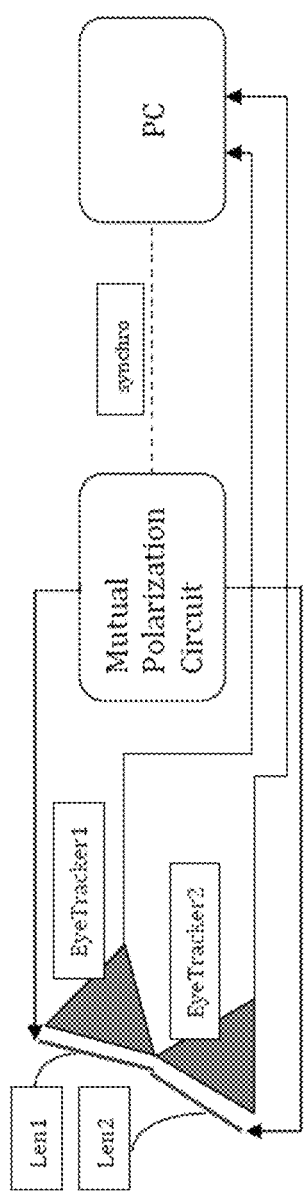
FIGS. 5 and 6 illustrate the components for a mechanism of mutual exclusion of the illuminator in an eye tracker architecture of the type described herein.

In some implementations, the mechanism of mutual exclusion shall be done by a couple of differently polarized lens (one per each eye tracker) properly excited by an electronic circuit synchronized with the acquisition PC. In this case, the sum of timing of lens excitation and settling time added to process and acquisition time will be considered as half of sampling time for each data stream by the acquisition PC. See FIG. 5.

Figure 6:
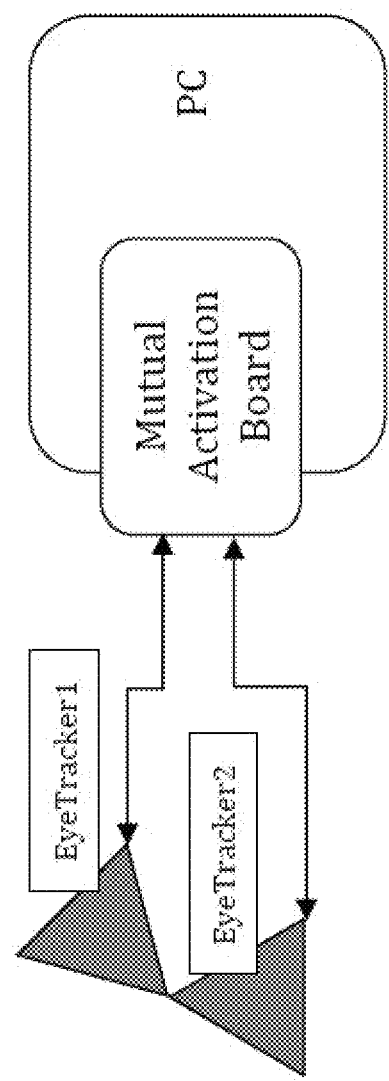

In some implementations, the clock time shall be output directly by a PC (or by a specific board) to one eye tracker by one. The device receiving the clock shall act as usual emitter and receiver of IR signal, the other shall be stopped. See FIG. 6.

Independently from the HW architecture, when the camera drive functionality is activated, the final data value from the system of eye trackers, is used by a PC to send the point of movement to the arm connected and which is holding the endoscopic camera.

Independently from the HW architecture, the PC shall use the final data value coming from the system of eye trackers to manage the controls of the software interface.

The concepts disclosed herein, particularly enhancing surgical robotics through the use of two eye trackers coordinated by a central algorithm, help to improve safety and reliability to the system, and more flexibility to the user in terms of where s/he moves or positions his/her head when using eye tracking.

What is claimed is:

1. A system for measuring an eye gaze to drive a robotic application, comprising;
    a monitor configured to display an image of surgical field to a user;
    a first eye tracker comprising a first pair of cameras defining a first head box, and a second eye tracker comprising a second pair of cameras defining a second head box, each of the first and second eye trackers configured to measure an eye movement of a user, wherein the first eye tracker and the second eye tracker are positioned to create an overlap region of the first head box and the second head box, at least one of the first eye tracker and the second eye tracker moveable relative to the other of the first eye tracker and the second eye tracker to increase or decrease a size of the overlap region;
    at least one processor with memory storing instructions executable by the processor to receive eye gaze input from each of the two eye trackers, calibrating and optimizing the eye gaze input from the eye trackers and for sending movement commands to a robotic manipulator arm holding an endoscopic camera or surgical instruments based on the eye gaze input.

2. The system of claim 1, wherein at least one of the first eye tracker and the second eye tracker is moveable relative to the monitor in a vertical or horizontal direction to capture a user/operator eye gaze point.

3. The system of claim 1, wherein at least one of the first eye tracker and the second eye tracker includes a polarizing filter.

4. The system of claim 1, wherein the memory includes instructions executable by the processor to remove the illumination interference from the first eye tracker from eye gaze input received from the second eye tracker during the eye gaze capture process.

* * * * *